United States Patent [19]

Fasman

[11] Patent Number: 5,523,295
[45] Date of Patent: Jun. 4, 1996

[54] METHOD FOR TREATING AND PREVENTING ALZHEIMER'S DISEASE

[75] Inventor: Gerald D. Fasman, Auburndale, Mass.

[73] Assignee: Brandeis University, Waltham, Mass.

[21] Appl. No.: 271,162

[22] Filed: Jul. 6, 1994

[51] Int. Cl.⁶ .......................... A61K 31/695; A61K 33/00
[52] U.S. Cl. ................................. 514/63; 424/724
[58] Field of Search .............................. 514/63; 424/724

[56] References Cited

U.S. PATENT DOCUMENTS

| | | | |
|---|---|---|---|
| 5,242,932 | 9/1993 | Gandy et al. | 514/313 |
| 5,385,915 | 1/1995 | Buxbaum et al. | 514/313 |

OTHER PUBLICATIONS

Edwardson J. A. et al, "Effect of Silicon on Gastrointestinal Absorption of Aluminum", Biosis, No. 93: 416445 (1993).

Fasman, G. D. and C. D. Moore, "The solubilization of model Alzheimer tangles: Reversing the β–sheet conformation induced by aluminum with silicates", Proc. Natl. Acad. Sci. USA, 91:11232–11235 (1994) (I).

Fasman, G. D. et al., "Solubilization of β–amyloid–(1–42)–peptide: Reversing the β–sheet conformation induced by aluminum with silicates", Proc. Natl. Acad. Sci. USA, 92:(in press) (1995) (II).

Schwarz, K. and D. B. Milne, "Growth–promoting Effects of Silicon in Rats", Nature, 239:333–334 (1972).

Perry, G. and M. A. Smith, "Senile Plaques and Neurofibrillary Tangles: What Role Do They Play in Alzheimer's Disease?", Clinical Neuroscience, 1:199–203 (1993).

Henig, R. M., "Is Misplacing Your Glasses Alzheimer's?", New York Times Magazine (Apr. 24, 1994).

Markeshery W. R. and W. D. Ehmann, "Aluminum and Alzheimer's Disease", Clinical Neuroscience, 1:212–218 (1993).

Goedert, M. et al., "Neurofibrillary tangles and β–amyloid deposits in Alzheimer's disease", Current Opinion in Neuro–biology, 1:441–447 (1991).

Edwardson, J. A. et al., "Aluminosilicates and the ageing brain: implications for the pathogenesis of Alzheimer's disease", Silicon Biochemistry, Ciba Foundation Symposium 121 (Ed. D. Evered and M. O'Connor), Wiley, pp. 160–179 (1986).

Naylor, G. J. et al., "Raised serum aluminum concentration in Alzheimer's disease", Trace Elements in Medicine, 6(3):93–95 (1989).

Banin, E. and H. Meiri, "Toxic Effects of Alumino–Silicates on Nerve Cells", Neuroscience, 39(1):171–178 (1990).

Martin, R. B., "Aluminosilicate Stabilities Under Blood Plasma Conditions", Polyhedron, 9(23):193–197 (1990).

Good, P. F. et al., "Selective Accumulation of Aluminum and Iron in the Neurofibrillary Tangles of Alzheimer's Disease: A Laser Microprobe (LAMMA) Study", Ann. Neurol., 31:286–292 (1992) (I).

Leterrier, J. F. et al., "A Molecular Mechanism for the Induction of Neurofilament Bundling by Aluminum Ions", J. Neurochem. 58:2060–2070 (1992).

Good, P. F. and D. P. Perl, "Aluminium in Alzheimer's?", Nature, 362:418 (1993) (II).

Eichhorn, G. L., "Is There Any Relationship Between Aluminum and Alzheimer's Disease?", Experimental Gerontology, 28:493–498 (1993).

Wisniewski, H. M. and G. Y. Wen, "Aluminium and Alzheimer's disease", Aluminium in biology and medicine, Ciba Foundation Symposium 169, Wiley, Chichester, pp. 142–164 (1992).

Lovell, M. A. et al., "Laser Microprobe Analysis of Brain Aluminum in Alzheimer's Disease", Ann. Neurol. 33:36–42 (1993).

Landsberg, J. P. et al., "Absence of aluminium in neuritic plaque cores in Alzheimer's disease", Nature, 360:65–68 (1992) (I).

Kruck, T. P. A., "Aluminium—Alzheimer's Link?", Nature, 363:119 (1993).

Landsberg, J. P. et al., "Alzheimer's response", Nature 364:294 (1993) (II).

Epstein, S. G., "Aluminum Intake and Its Effects", in Geochemistry and Health, Ed. I. Thornton et al., Science Reviews Ltd., Northwood; Antony Rowe Ltd.; Chippenham, Wiltshire, pp. 189–200 (1988).

Jones, K. C., "Human Exposure to Environmental Aluminium", in Geo–chemistry and Health, Ed. I. Thornton et al., Science Reviews Ltd., Northwood; Antony Rowe Ltd.; Chappenham, Wiltshire, pp. 243–244 (1988).

Flaten, T. P., "Geographical Associations between Aluminium in Drinking Water and Registered Death Rates with Dementia (including Alzheimer's Disease) in Norway", in Geochemistry and Health, Ed. I. Thornton et al., Science Reviews Ltd., Northwood; Antony Rowe Ltd.; Chappenham, Wiltshire, pp. 245–256 (1988).

Vogt, T., "A Possible Relationship between Aluminium in Drinking Water and Alzheimer's Disease in Southern Norway", in Geo–chemistry and Health, Ed. I. Thornton et al., Science Reviews Ltd., Northwood; Antony Rowe Ltd., Chippenham, Wiltshire, pp. 257–266 (1988).

Martyn, C. N. et al., "Geographical Relation Between Alzheimer's Disease and Aluminium in Drinking Water", The Lancet, pp. 59–62 (14 Jan. 1989).

McLachlan, D. R. Crapper et al., "Would decreased aluminum ingestion reduce the incidence of Alzheimer's disease?", Can. Med. Assoc. J. 145(7):793–804 (1991).

Doll, Sir Richard, "Review: Alzheimer's Disease and Environmental Aluminum", Age and Ageing, 22:138–153 (1993).

(List continued on next page.)

*Primary Examiner*—Allen J. Robinson
*Assistant Examiner*—Deborah Lambkin
*Attorney, Agent, or Firm*—Wolf, Greenfield & Sacks

[57] ABSTRACT

A method for treating or preventing Alzheimer's disease in a mammal is described. A silicon compound for inhibiting interaction between aluminum and β-amyloid or neurofilament protein is provided. The silicon compound is administered to a mammal in need of such treatment to cause this inhibition to occur.

14 Claims, 8 Drawing Sheets

OTHER PUBLICATIONS

Carlisle, E. M. et al., "Effect of Dietary Silicon and Aluminum on Silicon and Aluminum Levels in Rat Brain", Alzheimer Disease and Associated Disorders, 1(2):83–89 (1987).

Birchall, J. D., "The Toxicity of Aluminium and the Effect of Silicon on its Bioavailability", Aluminium in Chem. Biol. and Med., 1:53–69 (1991) (I).

Dobbie, J. W. and M. J. B. Smith, "Urinary and serum silicon in normal and uraemic individuals", Silicon Biochemistry, Ciba Foundation Symposium 121, (Ed. D. Evered and M. O'Connor), Wiley, pp. 194–213 (1986).

Hench, L. L. and J. Wilson, "Biocompatibility of silicates for medical use", Silicon Biochemistry, Ciba Foundation Symposium 121, (Ed. D. Evered and M. O'Connor), Wiley, pp. 231–246 (1986).

Misra, V. et al., "Binding of Silicic Acid by Proteins and its Relation to Toxicity of Silicate Dusts", J. Applied Toxicology, 3(3):135–138 (1983).

Birchall, J. D. and J. S. Chappell, "The Solution Chemistry of Aluminium and Silicon and Its Biological Significance", in Geo-chemistry and Health, Ed. I. Thornton et al., Science Reviews Ltd., Northwood; Antony Rowe Ltd.; Chippenham, Wiltshire, pp. 231–242 (1988) (II).

Birchall, J. D. and J. S. Chappell, "The Chemistry of Aluminum and Silicon in Relation to Alzheimer's Disease", Clin. Chem., 34(2):265–267 (1988) (III).

Berthon, G., "Relevance of aluminium-acid complex equilibria to aluminium bioavailability", Metal Ions in Biology and Medicine, 2:253–258 (1992).

Birchall, J. D., et al., "Acute toxicity of aluminium to fish eliminated in silicon-rich acid waters", Nature, 338:146–148 (1989) (IV).

Schehr, R. S., "Therapeutic Approaches to Alzheimer's Disease", Bio/Technology, 12:140–144 (1994).

Stevenson, R., "Drug leads begin to penetrate Alzheimer gloom", Chemistry in Great Britain, pp. 165–167 (1994).

Hanin, I., "A Survey of Current Treatment Strategies in Alzheimer's Disease," Drugs in Development, 2:195–200 (1993).

Owens, N. J., "Focus on tacrine HCl", Hosp. Formul., 28:679–688 (1993).

Birchall, J. D. and J. S. Chappell, "Aluminium, Water, Chemistry, and Alzheimers's Disease", The Lancet, p. 253, Apr. 29, 1989 (V).

Amberla, K. et al., "Long-term treatment with tacrine (THA) in Alzheimer's disease—evaluation of neuropsychological data", Acta Neurol. Scand., 149(S):55–57 (1993).

Maltby, N. et al., "Efficacy of tacrine and lecithin in mild to moderate Alzheimer's disease: double blind trail", BMJ, 308: 879–883.

Knapp, M. J. et al., "A 30-Week Randomized Controlled Trial of High-Dose Tacrine in Patients With Alzheimer's Disease", JAMA, 271:985–991 (1994).

Otvos, Jr., L. et al., "Phosphorylation Loops in Synthetic Peptides of the Human Neurofilament Protein Middle-Sized Subunit", J. Protein Chemistry, 7:365–376 (1988) (I).

Hollosi, M. et al., "Metal Ion-induced Conformational Changes of Phosphorylated Fragments of Human Neurofilament (NF-M) Protein", J. Mol. Biol. 223:673–682 (1992) (I).

Hollosi, M. et al., "$CA^{2+}$-Induced Conformational Transitions of Phosphorylated Peptides", Biopolymers, 33:497–510 (1993) (II).

Holly, S. et al., "FT-IR Spectroscopy Indicates that $Ca^{2+}$-Binding to Phosphorylated C-Terminal Fragments of the Midsized Neurofilament Protein Subunit Results in β-Sheet Formation and β-Aggregation," Biochemical and Biophysical Research Communications, 197:755–762 (1993).

Shen, Z. M. et al., "Study of $Al^{3+}$ Binding and Conformational Properties of the Alanine-Substituted C-Terminal Domain of the NF-M Protein and Its Relevance to Alzheimer's Disease", Biochemistry, 33:9627–9636 (1994).

Hollosi, M. et al., "Stable intrachain and interchain complexes of neurofilament peptides: A putative link between $Al^{3+}$ and Alzheimer disease", Proc. Natl. Acad. Sci. USA, 91:4902–9906 (1994) (III).

Otvos, Jr., L. et al., "Reversed-phase high-performance liquid chromatographic separation of synthetic phosphopeptide isomers", J. Chromatography, 512:265–272 (1990) (II).

Silica (Amorphous), in Kirk-Othmer Encyclopedia of Chemical Technology, Third Edition, vol. 20, Ed. H. F. Mark et al., John Wiley & Sons, New York, pp. 768–770 (1982).

Silicic Acid, in Cumulated Index Medicus, vol. 32, U. S. Dept. of Health and Human Services, NIH Publication No. 92-259, pp. 582, 12277 (1991).

GluGluLysGlyLysSer$^6$ProValProLysSer$^{11}$ProValGluGluLysGly (Seq. ID No. 1)

FIGURE 2

NF-M17 Ser⁶P:

GluGluLysGlyLysSer⁶ProValProLysSer¹¹ProValGluGluLysGly
                        |
                        PO3H2

(Seq. ID No. 2)

NF-M17 Ser¹¹P:

GluGluLysGlyLysSer⁶ProValProLysSer¹¹ProValGluGluLysGly
                                                |
                                          PO3H2

(Seq. ID No. 3)

NF-M17 Ser⁶PSer¹¹P:

GluGluLysGlyLysSer⁶ProValProLysSer¹¹ProValGluGluLysGly
                        |                        |
                       PO3H2         PO3H2

(Seq. ID No. 4)

AspAlaGluPheGlyHisAspSerGlyProGluValArgHisGln

LysLeuValPhePheAlaGluAspValGlySerAsnLysGlyAla

IleIleGlyLeuMetValGlyGlyValValIleAla (Seq. ID No. 5)

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( D ) TOPOLOGY: linear     ( x i ) SEQUENCE DESCRIPTION: SEQ ID NO:1:

Glu  Glu  Lys  Gly  Lys  Ser  Pro  Val  Pro  Lys  Ser  Pro  Val  Glu  Glu  Lys
    1                  5                              10                             15

Gly ( 2 ) INFORMATION FOR SEQ ID NO:2:

( i ) SEQUENCE CHARACTERISTICS:
        ( A ) LENGTH: 17 amino acids
        ( B ) TYPE: amino acid
        ( D ) TOPOLOGY: linear     ( i x ) FEATURE:

(A) NAME/KEY: serine is phosphorylated
(B) LOCATION: 6

(xi) SEQUENCE DESCRIPTION: SEQ ID NO:2:

Glu Glu Lys Gly Lys Ser Pro Val Pro Lys Ser Pro Val Glu Glu Lys
1               5                   10                  15

Gly (2) INFORMATION FOR SEQ ID NO:3:

(i) SEQUENCE CHARACTERISTICS:
    (A) LENGTH: 17 amino acids
    (B) TYPE: amino acid
    (D) TOPOLOGY: linear (ix) FEATURE:
    (A) NAME/KEY: serine is phosphorylated
    (B) LOCATION: 11

(xi) SEQUENCE DESCRIPTION: SEQ ID NO:3:

Glu Glu Lys Gly Lys Ser Pro Val Pro Lys Ser Pro Val Glu Glu Lys
1               5                   10                  15

Gly (2) INFORMATION FOR SEQ ID NO:4:

(i) SEQUENCE CHARACTERISTICS:
    (A) LENGTH: 17 amino acids
    (B) TYPE: amino acid
    (D) TOPOLOGY: linear (ix) FEATURE:
    (A) NAME/KEY: serines are phosphorylated
    (B) LOCATION: 6 and 11

(xi) SEQUENCE DESCRIPTION: SEQ ID NO:4:

Glu Glu Lys Gly Lys Ser Pro Val Pro Lys Ser Pro Val Glu Glu Lys
1               5                   10                  15

Gly (2) INFORMATION FOR SEQ ID NO:5:

(i) SEQUENCE CHARACTERISTICS:
    (A) LENGTH: 42 amino acids
    (B) TYPE: amino acid
    (D) TOPOLOGY: linear (xi) SEQUENCE DESCRIPTION: SEQ ID NO:5:

Asp Ala Glu Phe Gly His Asp Ser Gly Pro Glu Val Arg His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
                35                  40

METHOD FOR TREATING AND PREVENTING ALZHEIMER'S DISEASE

The U.S. Government has a paid-up license in this invention and the right in limited circumstances to require the patent owner to license others on reasonable terms as provided for by the terms of Grant No. 1-R01AG 10002-03 awarded by the National Institutes of Health.

FIELD OF THE INVENTION

This invention relates to treatment and prevention of Alzheimer's disease.

BACKGROUND OF THE INVENTION

Alzheimer's disease is the most prevalent form of senile dementia. Epidemiological studies suggest that 25-50% of all people in their 80's have Alzheimer's disease. There are about 4 million cases in the United States alone. Generally, the first symptom of Alzheimer's disease is memory loss, followed by a decline in reasoning ability and reduced use of speech. Behavioral disorders are also often present. The deterioration appears to be irreversible, and eventually leads to death. There is no effective treatment currently available.

A common feature of Alzheimer's disease and other neurodegenerative diseases is the accumulation of fibrous proteinaceous structures known as neurofibrillary tangles and senile plaques. Neurofilament (NF) protein is the main constituent of neurofibrillary tangles. NF proteins consist of three subunits based on molecular weight: high (NF-H), medium (NF-M) and low (NF-L). NF proteins form filaments via coiled-coil interactions between the structurally conservative rod sequences of NF-H, NF-M and NF-L. These filaments can give rise to neurofibrillary tangles when the NF protein is hyper-phosphorylated. β-amyloid, a protein containing about 42 amino acids, is the major component of senile plaque. β-amyloid can aggregate, giving rise to the plaques.

Many studies have shown that aluminum is found in neurofibrillary tangles and senile plaques. Aluminum can complex with β-amyloid or neurofilament protein. In addition, certain epidemiological studies indicate a link between aluminum in water supplies and the incidence of Alzheimer's disease.

SUMMARY OF THE INVENTION

It is an object of the invention to provide a safe, effective, easy and inexpensive method for treating or preventing Alzheimer's disease.

It is yet another object of the invention to provide a method for treating or preventing Alzheimer's disease which does not involve an invasive procedure.

It is yet another object of the invention to provide a simple method for treating or preventing Alzheimer's disease such as administering a pill, administering an injection or inserting an implant.

Still another object of the invention is to treat or prevent Alzheimer's disease by administering a silicon compound which inhibits interaction between aluminum and β-amyloid or neurofilament protein, so as to reduce or reverse formation of neurofibrillary tangles and/or senile plaques.

According to the invention, a method for treating or preventing Alzheimer's disease in a mammal is provided. A silicon compound is provided for inhibiting interaction between aluminum and β-amyloid or neurofilament protein. The silicon compound is administered to a mammal in need of such treatment to cause this inhibition to occur.

The silicon compound can be, e.g., a salt, e.g., sodium silicate, sodium metasilicate or silicon tetra acetate, an acid, e.g., silicic acid, an oxide, or combinations thereof.

In certain embodiments, the silicon compound inhibits interaction between aluminum and the neurofilament protein so as to at least partially prevent formation of, or to at least partially reverse a formed, neurofibrillary tangle. In other embodiments, the silicon compound inhibits interaction between aluminum and β-amyloid so as to at least partially prevent, or to at least partially reverse a formed, senile plaque.

Variations of this method of this invention include administering the silicon compound prior to formation of a neurofibrillary tangle or a senile plaque, administering the silicon compound subsequent to formation of a neurofibrillary tangle or a senile plaque, and administering the silicon compound to a human.

Another aspect of the invention is a method for treating or preventing Alzheimer's disease in a mammal in which a silicon compound for at least partially preventing a neurofibrillary tangle or a senile plaque is provided. The silicon compound is administered to a mammal in need of such treatment to cause this prevention to occur.

Yet another aspect of the invention is a therapeutic silicon compound in a dosage form and concentration suitable for treating or preventing Alzheimer's disease in a mammal in need of such treatment, the silicon compound being effective to inhibit interaction between aluminum and β-amyloid or neurofilament protein.

The above and other objects, features, and advantages of the present invention will be better understood from the following specification when read in conjunction with the accompanying drawings.

DETAILED DESCRIPTION

This invention provides a method for treating or preventing Alzheimer's disease in a mammal. A silicon compound is provided which inhibits interaction between aluminum and β-amyloid or neurofilament protein. The silicon compound is administered to a mammal in need of such treatment to cause this inhibition to occur.

Alzheimer's disease is a neurodegenerative condition which is meant to include the presence of cerebrocortical neurofibrillary tangles and/or senile plaques. Treating Alzheimer's disease is meant to include preventing, arresting, altering, and/or reversing formation of neurofibrillary tangles and/or senile plaques. By mammals is meant human as well as non-human mammals.

A silicon compound is meant to include any chemical species which contains silicon. Silicon compounds include, e.g., acids, salts and oxides. Preferably, the silicon compound is water soluble. By water soluble is meant a compound readily soluble in water at concentrations of mg/liter. A preferred acid is silicic acid, $H_4SiO_4$, which is a very weak acid, losing its first proton at a pKa of 9.6. The solubility of silicic acid in water or blood ranges from about 1.4 to about 2.2 mM. Free aluminum cations, $Al^{3+}$ can bind to silicic acid to yield the dialyzable species, $AlOSi(OH)_3^{2+}$, which, under physiological conditions results in hydroxyaluminosilicate. Preferably, a silicic acid concentration of about 100 μm or greater is used to complex aluminum. Such complexing renders the aluminum unreactive in a variety of physiological environments. Silicic acid is capable of binding to aluminum already bound to neurofibrillary tangles and/or β-amyloid and extracting it, causing solubilization of the precipitated protein or peptide.

Examples of silicon salts include sodium silicate, e.g., 2:1 or 3:1, sodium metasilicate and silicon tetra acetate. Preferably, soluble silicon salts are used. Free aluminum cations, $Al^{3+}$ can bind to the silicon salts to yield aluminum silicates. Silicon salts can also bind to neurofibrillary tangles and/or β-amyloid and extract it, causing solubilization of the precipitated protein or peptide. Silicon salts are preferred in this invention.

The silicon compound of this invention is able to inhibit interaction between aluminum and β-amyloid or neurofilament protein. The term inhibit interaction is meant to include inhibition which occurs either before or after the aluminum complexes with β-amyloid or neurofilament protein. For example, the silicon compound can complex with free aluminum, thereby preventing free aluminum from interacting with β-amyloid or neurofilament proteins. In other embodiments, the silicon compound can complex with aluminum that is already bound to β-amyloid or neurofilament protein, thereby removing the aluminum from the β-amyloid or neurofilament proteins. Inhibition includes partial or complete inhibition.

The silicon compound is administered so as to treat or prevent the formation of neurofibrillary tangles and/or senile plaques. In persons with Alzheimer's disease, the β-amyloid and neurofilament proteins found in the senile plaques and neurofibrillary tangles are generally phosphorylated and complexed with aluminum, and assume a β-sheet structure. Peri, D., in "Metal Ions in Biological Systems," Vol. 24, eds. Sigel & Sigel, Marcel Dekker Ins., N.Y. (1988), pp. 259–283. It is the B-sheet structure which causes these proteins to become insoluble and to precipitate out, thereby giving rise to the tangles and plaques.

Examples 1 and 2 illustrate that a silicon compound can reverse the structural alterations that result from the addition of aluminum to neurofilament protein (NF-M17) (Seq. ID No. 1) and β-amyloid (Seq. ID No. 5). β-amyloid (Seq. ID No. 5) and neurofilament (NF-M17) protein (Seq. ID No. 1) each normally exhibit a partial α-helical structure. Upon the addition of aluminum, β-sheet structures are formed. If a silicon compound is also added, the proteins are transformed back to their original partial α-helical structure. These results were obtained for both phosphorylated and non-phosphorylated proteins. If citrate is added instead of a silicon compound, The proteins are not transformed back to their original structure.

Administration of the silicon compound can be accomplished by any method which allows the silicon compound to reach its target. By target is meant the place where the silicon compound is able to inhibit interaction between aluminum and β-amyloid or neurofilament proteins. This inhibition can occur before or after the aluminum complexes with the β-amyloid or neurofilament proteins. Examples of targets include the gastrointestinal tract, the blood stream and the brain.

The administration methods include, e.g., injection, deposition, implantation, suppositories, oral ingestion, inhalation, topical administration, or any other method of administration where access to the target by the silicon compound is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the silicon compound with an aerosol in an inhalator, either alone or attached to a carrier that can be absorbed.

The silicon compound can be suspended in a liquid, e.g., in dissolved form or colloidal form. The liquid can be a solvent, partial solvent or non-solvent. In many cases water or an organic liquid can be used.

Administration of the silicon compound can be alone or in combination with other therapeutic agents. In certain embodiments, the silicon compound can be combined with a suitable carrier, incorporated into a liposome, or incorporated into a polymer release system. Silicon compounds have been demonstrated to be biocompatible. Hench et al., in "Silicon Biochemistry," Ciba Foundation Symposium #121, eds. Everst & O'Conner, John Wiley & Sons (1988).

In certain embodiments of the invention, the administration can be designed so as to result in sequential exposures to the agent over some time period, e.g., hours, days, weeks, months or years. This can be accomplished by repeated administrations of the silicon compound by one of the methods described above, or alternatively, by a controlled release delivery system in which the silicon compound is delivered to the mammal over a prolonged period without repeated administrations. Administration of such a system can be, e.g., by long acting oral dosage forms, bolus injections, transdermal patches and sub-cutaneous implants. Maintaining a fairly constant level of the silicon compound is preferred so as to allow for scavenging aluminum throughout the body and promoting its excretion via the kidney and bowel. Avoiding short-term elevated levels of silicon is preferred in order to minimize the precipitation of silicate kidney stones in the presence of high non-physiological levels of silicon compounds.

The silicon compound can be administered prior to or subsequent to neurofibrillary tangle and/or senile plaque formation. In certain embodiments, the silicon compound is administered to persons who have a family history of Alzheimer's disease, or who have a genetic predisposition for the disease. In other embodiments, the silicon compound is administered to persons who have reached a particular age and who therefore are more likely to get the disease. In yet other embodiments, the silicon compound is administered to persons who exhibit either early or advanced symptoms of the disease. The silicon compound can also be administered to persons as a preventive measure.

The silicon compound is administered to the mammal in a therapeutically effective amount. By therapeutically effective amount is meant that amount which is capable of at least partially preventing or reversing neurofibrillary tangle and/or plaque formation. A therapeutically effective amount can be determined on an individual basis and will be based, at least in part, on consideration of the species of mammal, the mammal's size, the silicon compound used, the type of delivery system used, the time of administration relative to tangle or plaque formation, and whether a single, multiple, or controlled release dose regimen is employed. A therapeutically effective amount can be determined by one of ordinary skill in the art employing such factors and using no more than routine experimentation.

Preferably, the concentration of the silicon compound is at a dose of about 0.1 m moles/liter to about 50 m moles/liter. Most preferably the dose is about 0.5 m moles/liters to about 5.0 m moles/liter. The specific concentration partially depends upon the particular silicon compound used, as some are more effective than others. The dosage concentration of the silicon compound that is actually administered is dependent at least in part upon the final concentration that is desired at the site of action, the method of administration, the efficacy of the particular silicon compound, the longevity of the particular silicon compound, and the timing of administration relative to the formation of the tangles and/or plaques. Preferably, the dosage form is such that it does not substantially deleteriously affect the mammal. The dosage can be determined by one of ordinary skill in the art employing such factors and using no more than routine experimentation.

The invention also includes a therapeutic silicon compound in a dosage form and concentration suitable for treating or preventing Alzheimer's disease in a mammal in need of such treatment, the silicon compound being effective to interfere with interaction between aluminum and β-amyloid or neurofilament protein.

EXAMPLES

Example 1

β-Sheet Formation of Phosphorylated and Non-Phosphorylated Neurofilament Mid-Sized Protein (NF-M17) by the Addition of $Al^{3+}$ and Reversibility by the Addition of Silicate This example illustrates that the partial α-helical structure of phosphorylated and non-phosphorylated 17 amino acid fragments of the human neurofilament mid-sized protein (NF-M17) (Seq. ID No. 1) forms β-sheets upon the addition of $Al^{3+}$, and that these β-sheets are substantially transformed back to the original partial α-helical structure upon the addition of $SiO_4^{4-}$.

Figure 1:
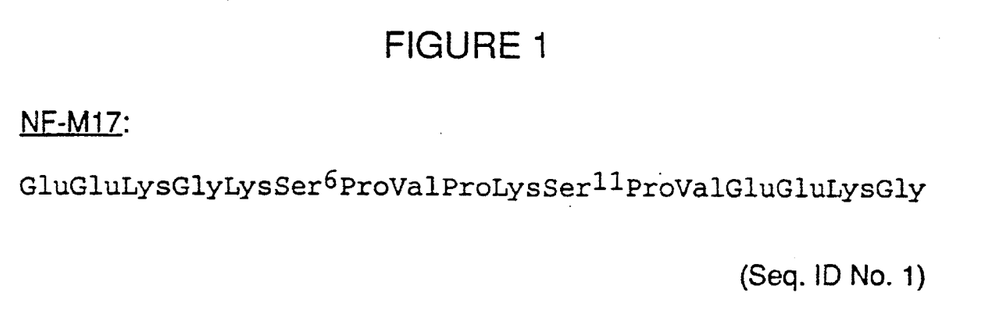
FIG. 1 depicts the amino acid sequence of a 17 amino acid peptide from the human neurofilament mid-sized subunit protein (NF-M17) (Seq. ID No. 1).
Figure 2:
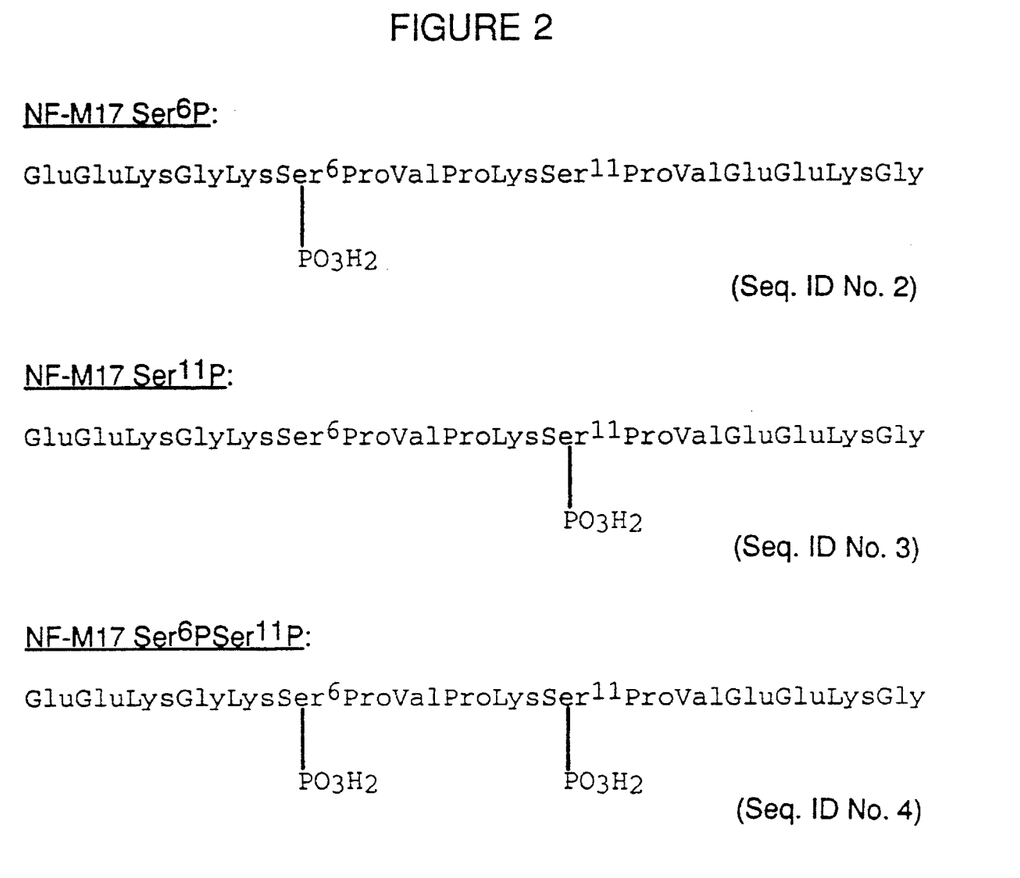
FIG. 2 depicts three phosphorylated derivatives (Seq. ID Nos. 2, 3 and 4) of the NF-M17 peptide (Seq. ID No. 1) shown in FIG. 1.

Peptides containing a seventeen amino acid region of the human neurofilament mid-sized subunit protein (NF-M17) were synthesized as previously described (Hollosi et al., J. Mol. Biol., 223:673–682 (1992)). FIG. 1 shows the sequence of the NF-M17 peptide (Seq. ID No. 1). After synthesis of the 17 amino acid fragment, the serines, at amino acid residue positions 6 and 11, were phosphorylated using the poly-phosphoric acid method reported by Otvos et al., J. Chromatogr. 512:265–272 (1990). The reaction was allowed to proceed for 2–3 days, after which time the reaction was neutralized and the phosphorylated products and starting material were separated using HPLC. FIG. 2 shows the three phosphorylated peptides that were produced, NF-M17 Ser$^6$P (Seq. ID No. 2), NF-M17 Ser$^{11}$P (Seq. ID No. 3) and NF-M17 Ser$^6$PSer$^{11}$P (Seq. ID No. 4).

2,2,2-trifluorethanol (TFE) (NMR grade) and aluminum nonahydrate were obtained from Aldrich, Milwaukee, Wis., sodium silicate was obtained from Johnson Matthey Catalog Corporation, Ward Hill, Mass. Circular dichroic (CD) spectra were acquired using a J-Y Mark V Circular Dicrograph, I.S.A. Jobin Yvon, Longjumeau, France.

For the CD titrations the peptides were dissolved in TFE to a concentration between 0.4–0.18 mg/ml. The $Al^{3+}$ solutions (33 or 36 mM) were prepared in TFE, and $Na_4SiO_4$ was dissolved in water (136 mM). Initial spectra contained only peptide. Incremental additions of $Al^{3+}$ solution were made until 8 or 16 molar equivalents of metal ion were added to the peptide. Once the maximum conformational change was reached, $SiO_4^{4-}$ was titrated into the curvette. Additions were made as increments of peptide molar equivalents and did not exceed 32 equivalents. The conformational influence of each addition was monitored by CD.

A conformational transition of the non-phosphorylated MF-17 peptide (Seq. ID No. 1) from partially α-helical structure to one that contained B-sheet upon addition of $Al^{3+}$ was observed. Continued addition of $Al^{3+}$ resulted in precipitation of the peptide. These results are in agreement with previous studies by Hollosi et al., J. Mol. Biol. 223:673–682 (1992). The addition of $SiO_4^{4-}$ resulted in a CD spectrum similar to the initial partially α-helical structure.

Figure 3:
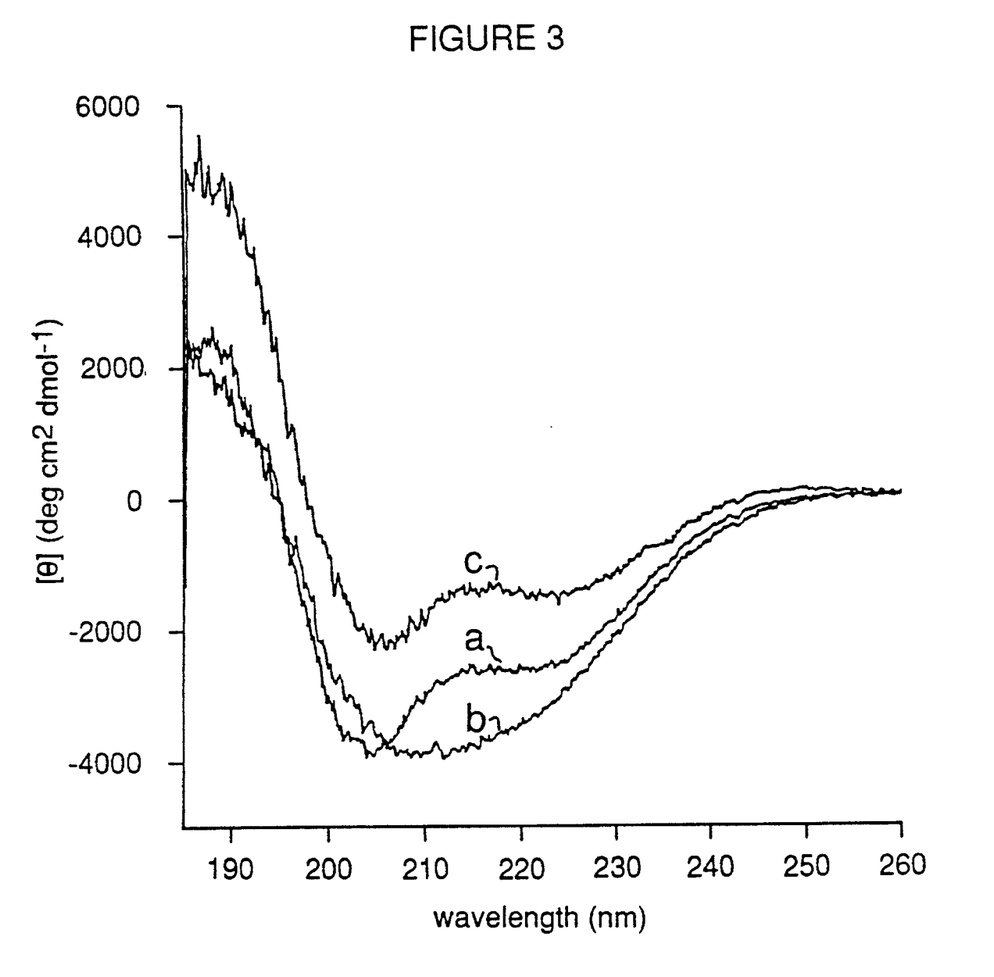
FIG. 3 depicts circular dichroic (CD) spectra of NF-M17 (Seq. ID No. 1) resulting from titration with $Al^{3+}$ and $SiO_4^{4-}$.

The reversibility of the NF-M17/$Al^{3+}$ titration is shown in FIG. 3. The NF-M17 peptide (Seq. ID No. 1) was titrated with 16 molar equivalents of $Al^{3+}$ beginning at 2 equivalents. The initial curve (curve a) showed a peak at 190 nm and a trough at 204 nm with a shoulder at 220 nm. Each addition of $Al^{3+}$ resulted in a gradual "shallowing" of the deep trough and a deepening of the shoulder, a curve characteristic of a B-sheet, curve b. With each addition of $SiO_4^{4-}$, the curve gradually returned to its original shape. No significant change was noted with the first few titration points, however, when the titration approached equal molar quantities of $SiO_4^{4-}$ and $Al^{3+}$, significant changes were noted. A spectrum similar to the initial one was observed, curve c. Twelve hours later, the same spectrum was obtained. As a control experiment, the NF-M17 peptide was titrated with just $SiO_4^{4-}$ ion to see if this had any effect on The native spectrum. Minor changes were observed: a slight rise in the baseline from 0 degrees and an increase in the peak intensity at 195 nm. These results may imply an increase in random coil content, although the overall shape of the curve was very similar to that of NF-M17 with nothing added.

Figure 4:
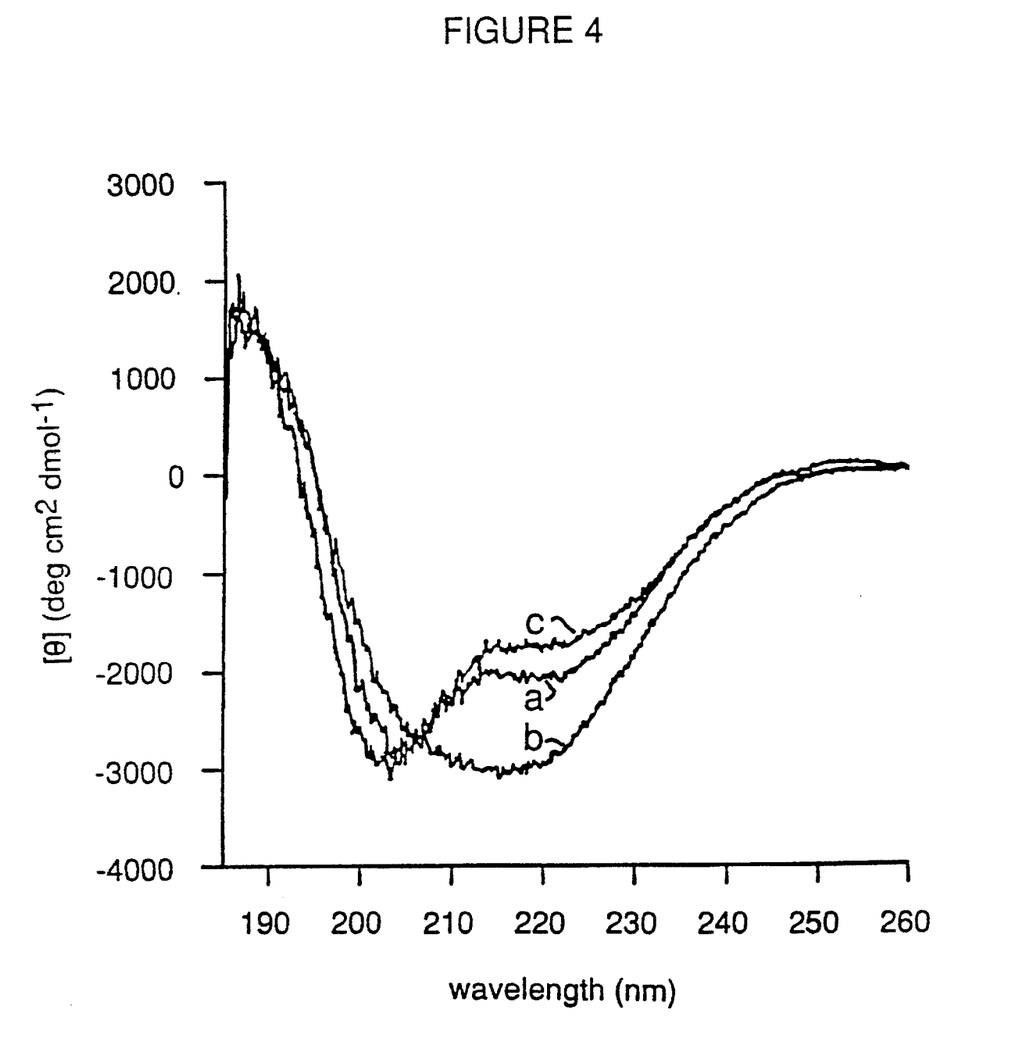
FIG. 4 depicts CD spectra of NF-M17 $Ser^6P$ (Seq. ID No. 2) resulting from titration with $Al^{3+}$ and $SiO_4^{4-}$.

Titrations were also done with the NF-M17 phosphorylated derivatives. NF-M17 Ser$^6$P (Seq. ID No. 2), NF-M17 Ser$^{11}$P (Seq. ID No. 3), and NF-M17 Ser$^6$PSer$^{11}$P (Seq. ID No. The presence of phosphate groups attached to the peptides induces much stronger binding to aluminum. The negative $PO_4^{3-}$ ion binds to the positively charged $Al^{3+}$ ion. The results of the reversibility titration for NF-M17 Ser$^6$P peptide (Seq. ID No. 2) are illustrated in FIG. 4. The initial spectrum is shown as curve a. This peptide was converted to a β-sheet with 4 molar equivalents of $Al^{3+}$ (curve b). At equal concentrations of $SiO_4^{4-}$ and $Al^{3+}$ the peptide spectrum began to resemble the original spectrum but the 195 nm trough was not as deep. Twice as much $SiO_4^{4-}$ as $Al^{3+}$ resulted in a spectrum which had a shallower shoulder at 220 nm and a deeper trough at 204 nm (curve c).

Figure 5:
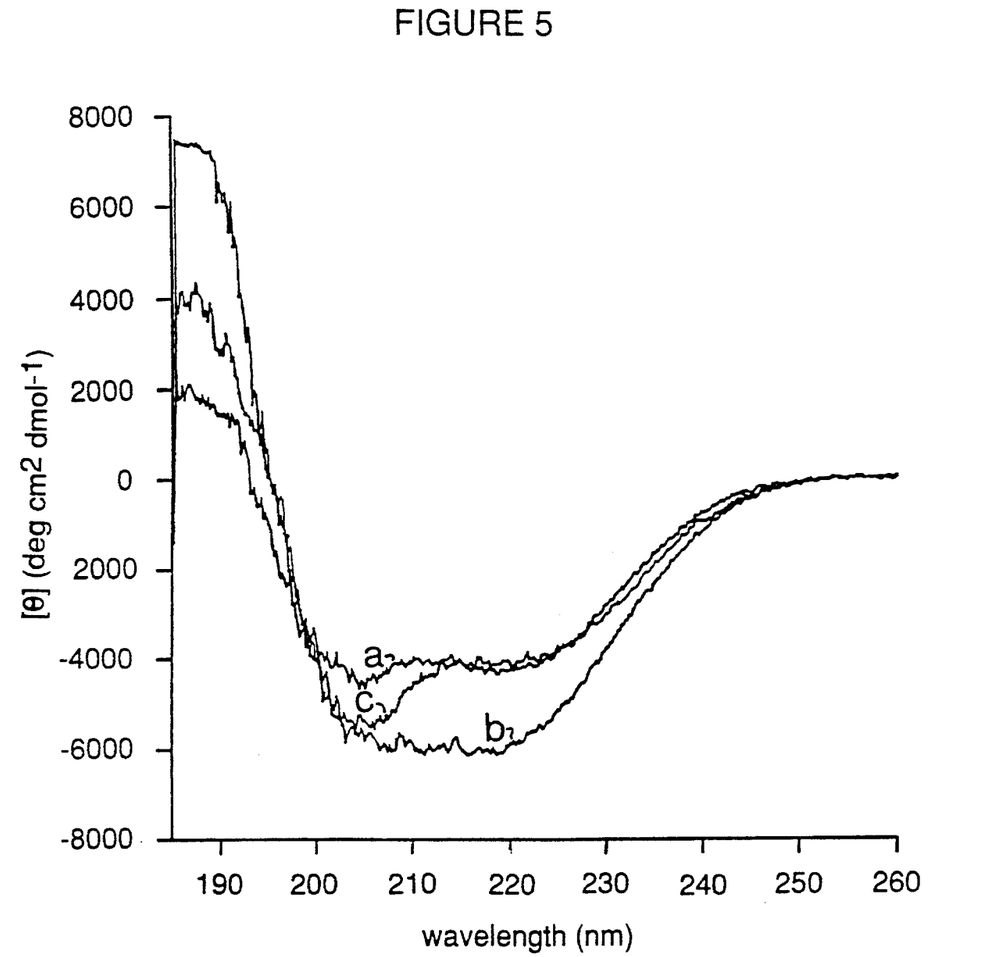
FIG. 5 depicts CD spectra of NF-M17 $Ser^{11}P$ (Seq. ID No. 3) resulting from titration with $Al^{3+}$ and $SiO_4^{4-}$.

Titration of the NF-M17 Ser[11]P peptide (Seq. ID No. 3) is shown in FIG. 5. The initial spectrum is shown as a curve a. After 16 molar equivalents of $Al^{3+}$ the metal ion titration was complete, curve b. Reversibility of the $Al^{3+}$ effects required only equal molar quantities of $SiO_4^{4-}$ ion, curve c. These solution conditions resulted in a spectrum with more random character than the original spectrum.

Figure 6:
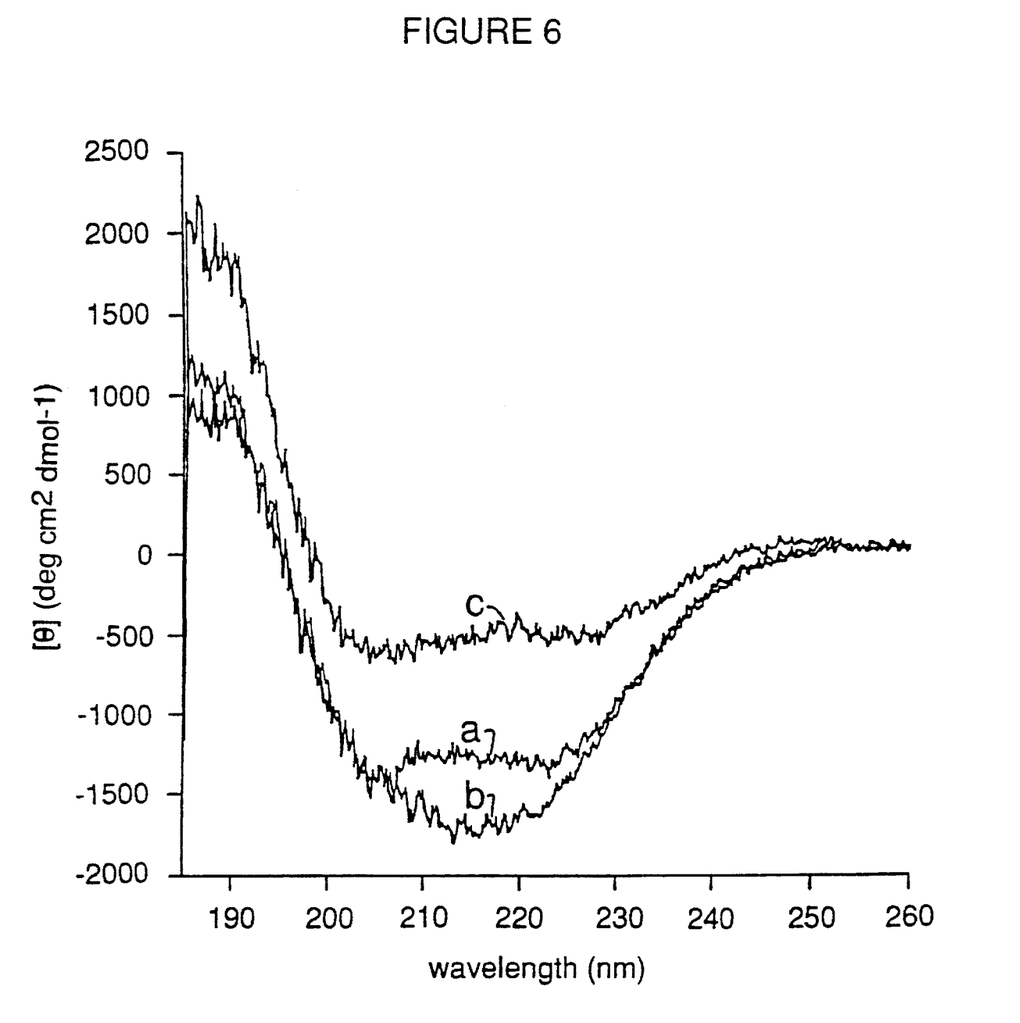
FIG. 6 depicts CD spectra of NF-M17 $Ser^6PSer^{11}p$ (Seq. ID No. 4) resulting from titration with $Al^{3+}$ and $SiO_3^{4-}$.

The NF-M17 Ser[6]PSer[11]P peptide (Seq. ID No. 4) as shown in FIG. 6, curve a, was titrated with 8 molar equivalents of $Al^{3+}$, shown in curve b. It required twice as much $SiO_4^{4-}$ ion to obtain a spectrum, curve c, which resembled the lone peptide. Although all of these titrations gave a more random coil-like spectrum, they were much more similar to the initial peptide spectrum than to that of the $Al^{3+}$ bound species.

Figure 7:
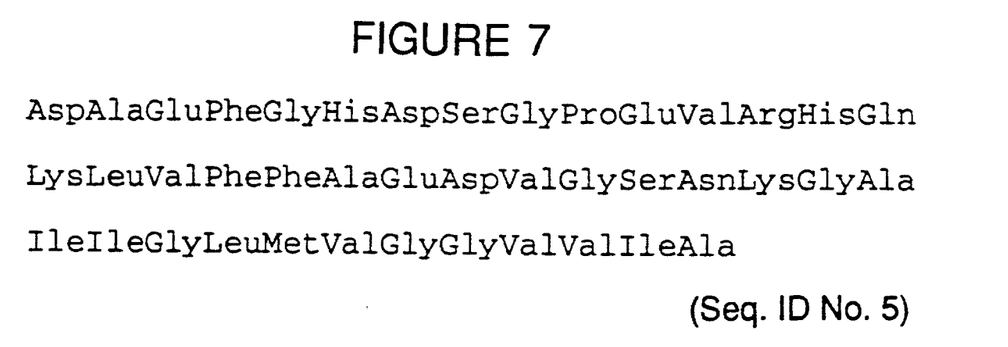
FIG. 7 depicts the amino acid sequence of rat A42 β-amyloid (Seq. ID No. 5).

Example 2

β-Sheet Formation of β-Amyloid A42 Polypeptide by the Addition of $Al^{3+}$ and Reversibility by the Addition of Silicate This example illustrates that the partial α-helical structure of rat A42 β-amyloid protein (Seq. ID No. 5) forms β-sheets upon the addition of $Al^{3+}$ and that these β-sheets are transformed back to the original partial α-helical structure upon the addition of $SiO_4^{4-}$. The titration of A42 β-amyloid protein (Seq. ID No. 5) from rat, shown in FIG. 7, was performed with a 0.39 mg/mL solution; the solvent was TFE. The $Al^{3+}$ solution (41.6 mM) was prepared in TFE, and the $Na_4SiO_4$ was dissolved in water (138 mM). The initial CD spectrum examined the conformation of protein only; incremental additions of $Al^{3+}$ solution (4.25 μL/molar equivalent) were made until 4 molar equivalents of metal ion were reached. After a conformational change was noted as monitored by CD, $SiO_4^{4-}$ (1.28 μL/molar equivalent) was titrated into the curvette until the CD spectrum approximated that of the original. This point was reached at a 1:1 ratio of $Al^{3+}:SiO_4^{4-}$.

Figure 8:
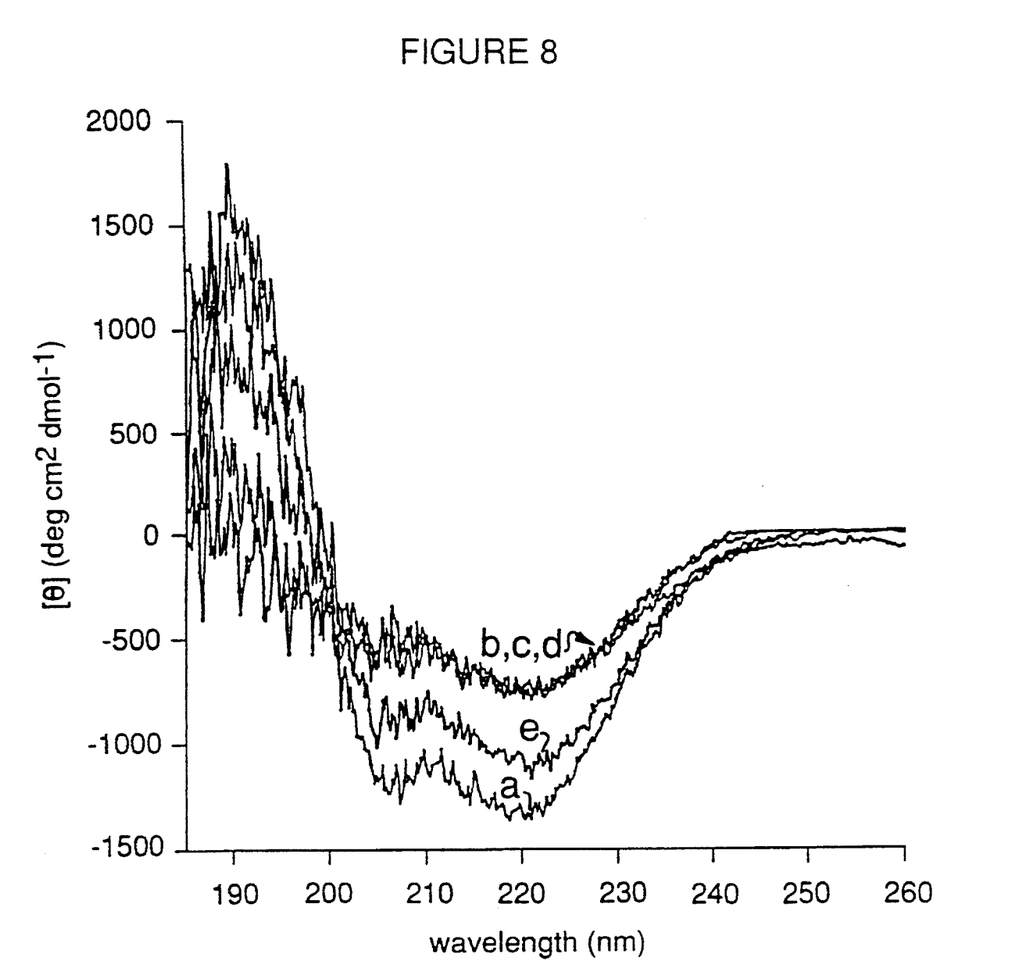
FIG. 8 depicts CD spectra of rat A42 β-amyloid (Seq. ID No. 5) resulting from titration with $Al^{3+}$ and $SiO_4^{4-}$.

The results of the titration of the rat A42 β-amyloid protein (Seq. ID No. 5) are shown in FIG. 8. A42 in TFE without $Al^{3+}$ or $SiO_4^-$ is shown in curve a. This curve demonstrates a partial α-helical structure. Upon addition of 2 molar equivalents of $Al^{3+}$ the $[\Theta]_{220}$ increased, indicating the formation of β-sheets (curve b). On addition of 4 equivalents of $Al^{3+}$ the curve (curve c) remained identical to that of curve b. Two mole equivalents of $SiO_4^{4-}$ added to the solution (curve d) caused no change in structure. However, addition of 4 equivalents of $SiO_4^{4-}$ produced curve e. Thus, a reverse of the effect of $Al^{3+}$ was brought about by the addition of $SiO_4^{4-}$. The A42 β-amyloid protein, which was transformed into β-sheets by the addition of $Al^{3+}$ was transformed into its initial conformation by the addition of $SiO_4^{4-}$.

Example 3

Treating Alzheimer's Disease in a Human

This example illustrates a method for treating Alzheimer's disease in a human with a silicon compound which inhibits interaction between aluminum and β-amyloid, and aluminum and neurofilament protein. The patient is given sodium silicate orally, in the form of a pill, once a day. The dose concentration per day is 4.0 m moles/liter. Administration is carried out for a period of six months. This treatment interferes with further development of neurofibrillary tangles and senile plaques.

Those skilled in the art will be able to ascertain, using no more than routine experimentation, many equivalents of the specific embodiments of the invention described herein. These and all other equivalents are intended to be encompassed by the following claims.

I claim:

1. A method for treating or preventing Alzheimer's disease in a mammal, comprising:
    providing a silicon compound capable of inhibiting interaction between aluminum and β-amyloid or neurofilament protein; and
    administering said silicon compound to a mammal in need of such treatment to cause such inhibition to occur.

2. The method of claim 1 wherein said silicon compound is selected from the group consisting of a salt, an acid, an oxide, and combinations thereof.

3. The method of claim 1 wherein said silicon compound is a salt selected from the group consisting of sodium silicate, sodium metasilicate, silicon tetra acetate, and combinations thereof.

4. The method of claim 1 wherein said silicon compound is a silicate.

5. The method of claim 1 wherein said silicon compound inhibits interaction between said aluminum and said neurofilament protein so as to at least partially prevent formation of a neurofibrillary tangle.

6. The method of claim 1 wherein said silicon compound inhibits interaction between said aluminum and said β-amyloid so as to an least partially prevent formation of a senile plaque.

7. The method of claim 1 wherein said silicon compound inhibits interaction between said aluminum and said neurofilament protein so as to at least partially reverse a formed neurofibrillary tangle.

8. The method of claim 1 wherein said silicon compound inhibits interaction between said aluminum and said β-amyloid so as to at least partially reverse a formed senile plaque.

9. The method of claim 1 wherein said administering occurs prior to formation of a neurofibrillary tangle.

10. The method of claim 1 wherein said administering occurs prior to formation of a senile plaque.

11. The method of claim 1 wherein said administering occurs subsequent to formation of a neurofibrillary tangle.

12. The method of claim 1 wherein said administering occurs subsequent to formation of a senile plaque.

13. The method of claim 1 wherein said mammal is a human.

14. A method for treating or preventing Alzheimer's disease in a mammal comprising:

provoding a silicon compound capable of at least partially preventing formation of a neurofibrillary tangle or a senile plaque; and administering said silicon compound to a mammal in need of such treatment to cause said prevention to occur.

* * * * *